(12) United States Patent
Busch, Jr.

(10) Patent No.: US 6,200,553 B1
(45) Date of Patent: Mar. 13, 2001

(54) FINGERNAIL HARDENING TREATMENT

(76) Inventor: Francis W. Busch, Jr., 378 Luther Dr., Southbury, CT (US) 06488

( * ) Notice: Subject to any disclaimer, the term of this patent is extended or adjusted under 35 U.S.C. 154(b) by 0 days.

(21) Appl. No.: 09/303,393

(22) Filed: May 1, 1999

(51) Int. Cl.[7] ............................... A61K 7/04; A61K 7/043
(52) U.S. Cl. ............................................. 424/61; 427/2.13
(58) Field of Search ............................... 424/61; 427/2.13

(56) References Cited

U.S. PATENT DOCUMENTS 4,880,660 * 11/1989 Aasen et al. .
4,919,920 * 4/1990 Devos .
5,478,551 * 12/1995 Busch .
5,525,648 * 6/1996 Aasen et al. .

* cited by examiner

*Primary Examiner*—Thurman K. Page
*Assistant Examiner*—Amy E Pulliam

(57) ABSTRACT

The application of a soluble calcium compound and the further application of a suitable fluoride material accomplish calcium remineralization of fingernails. The calcium and fluoride preparations are kept separate until used. The calcium preparation is rubbed into the nail prior to the application of the fluoride; the fluoride then combines with the calcium applied in the first step within the nail allowing the nail to become harder and stronger.

9 Claims, No Drawings

FINGERNAIL HARDENING TREATMENT

BACKGROUND OF THE INVENTION

The fingernail is composed primarily of hard keratin, which is a mixture of proteins hardened by its calcium content and disulfide bonding. An excellent review of the fingernail chemistry appears in the Archives of Dermatology—Vol. 94,November 1966. This article confirms the effect of calcium on nail hardness.

Fluorides have been used extensively to increase the hardness of nails. Teeth have long benefited from the topical application of fluoride typically applied directly from toothpaste. It is generally believed that the effectiveness of fluoride in strengthening teeth, bone or nails results from the formation of insoluble calcium fluoride compounds where the source of the calcium exist naturally in the structure being treated. Nails contain calcium naturally. Busch (the current inventor) discloses in U.S. Pat. No. 5,478,551 that the physical strength of nails can be increased by applying fluoride solutions thereto.

It is believed that fluoride treatment of teeth, bone and fingernails is effective because these materials naturally contain the necessary calcium available for combination with fluoride.

The fingernail contains the least amount of natural calcium of the group consisting of bone, teeth and fingernails. While the calcium content of teeth and bone exceed 20% in various forms; the calcium content of fingernails is about 0.1%.

Various calcium treatment products for increasing the calcium content of fingernails in order to strengthen them exist in the current marketplace. Typical products of this type contain calcium compounds dispersed in a nitro cellulose lacquer. No specific claims are made for the calcium compounds and it is generally understood that the strengthening benefit is derived primarily from the lacquer coating.

The cells that make up the nail structure are dead, and it is unlikely that calcium in this form provides a significant benefit to the nail.

None of the calcium products in the current art are known to permanently strengthen the nail. There are no prior art references for increasing the calcium content of the fingernail known to the present inventor.

The present invention is directed toward increasing the amount of calcium in the nail thereby increasing the effectiveness of fluoride as a strengthening agent thereby increasing the strength of the nail.

SUMMARY OF THE INVENTION

It is a primary object of this invention to provide a new and improved process wherein additional inorganic calcium compounds are precipitated within fingernails, thereby increasing fingernail strength.

Another object is to provide a new and improved process for increasing the calcium content of fingernails so that these fingernails can be further strengthened by farther treatment with a suitable fluoride composition.

These and other objects and advantages of this invention will either be explained or will become apparent hereinafter.

In accordance with the principles of the present invention, low calcium levels in the nail are increased by applying to the nail, compositions in two phases which are kept separate until application to the nail. One phase contains a calcium compound dissolved in water, glycerin, or an organic solvent and a second phase contains a fluoride compound dissolved in a suitable solvent usually water or anhydrous ethyl alcohol.

The calcium phase is applied to the nail and allowed to penetrate into the nail keratin. The fluoride compound is next applied, causing an insoluble calcium fluoride material to be precipitated within the nail keratin causing a dramatic increase in the strength of the fingernail.

It has been found that calcium levels can be effectively increased in this manner but the calcium must be prevented from the reaction with the fluoride ion until immediately prior to use or applied separately to the nail. A second method may be used whereby the fluoride solution is first applied to the nail followed by application of the calcium solution. When this latter method is used, it may be necessary to reapply a further amount of the fluoride solution to react with any excess calcium ion.

DETAILED DESCRIPTION OF PREFERRED EMBODIMENTS

The calcium compounds of this invention are soluble salts, which can be applied from a cream or as a simple solution. When solutions of the calcium salts of this invention are used, the solvents are usually but not limited to water, glycerin, alcohol, propylene glycol, or a mixture of the four. Anhydrous ethyl alcohol or water are the preferred solvents employed in this invention.

Particularly useful calcium compounds of this invention are calcium acetylsalicylate, calcium ascorbate, calcium chloride, calcium citrate, calcium cyclamate, calcium gluconate, calcium glycerophosphate, calcium 2-ethylbutanoate, calcium methonate, calcium pantothenate, calcium phenosulfonate, calcium propionate, calcium nitrate, calcium sulfate and calcium hydroxide. Calcium chloride and calcium nitrate are the preferred calcium The fluorides useful for this invention are those currently used in dental products. Suitable Fluoride compounds include the alkali metal fluorides such as sodium fluoride, lithium fluoride, or potassium fluoride. Also suitable are ammonium fluoride, stannous fluoride, zirconium fluoride, or nickel fluoride. The water soluble alkali metal monofluorophosphates such as sodium, lithium, or potassium monofluorophosphate are useful for this invention.

Particularly useful is ammonium hexafluorophosophate because of its solubility in ethyl alcohol. Ammonium hexafluorophosphate is the preferred fluoride employed in this invention.

The calcium compounds of this invention may be applied to the nail in the form of a cream or as a solution. When a cream is used it would be made accordance with the principles of cosmetic emulsion technology well know in the art. These principals are well explained in standard reference books. A good example is chapter thirty-eight titled EMULSIONS in Harrys' Cosmeticology seventh edition Chemical Publishing Co., Inc. New York, N.Y. 10011.

When a cream is used as a carrier for the calcium ingredient of this invention, the calcium ingredient would be first dissolved in the water phase.

EXAMPLES OF PREPARING CALCIUM IN CREAM FORM

The following examples of such a cream are as follows shown in parts per weight: There are four examples each being a different vertical column numbered 1 through 4 respectively.

|  | 1 | 2 | 3 | 4 |
|---|---|---|---|---|
| Water Phase |  |  |  |  |
| De-ionized water | 79.51 | 81.41 | 79.91 | 72.01 |
| Methylparaben | .1 | .1 | .1 | .1 |
| Propylene Glycol | 5.00 | 5.0 | 5.0 | 5.0 |
| Glycerin | 3.00 | 3.0 | 3.0 | 3.0 |
| Calcium chloride | 2.00 | .50 | .10 | 5.0 |
| Calcium Pantothenate | .50 | .10 | 2.00 | 5.0 |
| Imidazolidinyl Urea | .50 | .5 | .5 | .5 |
| Oil Phase |  |  |  |  |
| Cetearyl Alcohol and Cetearth 20 | 1.5 | 1.5 | 1.5 | 1.5 |
| Cetearyl Alcohol | 1.5 | 1.5 | 1.5 | 1.5 |
| Glyceryl Stearate | 1.5 | 1.5 | 1.5 | 1.5 |
| Triceteareth-4 Phosphate | .42 | .42 | .42 | .42 |
| Propylparaben | .20 | .20 | .20 | .20 |
| Myristyl Octanoate | 4.27 | 4.27 | 4.27 | 4.27 |

The Cetearyl alcohol and cetearth 20 is a commercial blend of ingredients sold by The Amerchol corporation under the trade name Promuldgen D. The other ingredients are standard cosmetic ingredients widely used and well known in the art and are used for their normal purpose in forming an acceptable cosmetic cream. Various concentrations of the calcium salts of this invention are demonstrated to effectively increase the content of the calcium content in the nail when first applied to the nail followed by an application of fluoride.

The preferrred calcium phases of this invention are solutions of calcium in water or ethyl alcohol. Ethyl alcohol is preferred because it is easier to apply and dries faster. The following examples of such solutions are as follows shown in parts per weight: There are four examples each being a different vertical column numbered 5 through 8 respectively

EXAMPLES OF PREPARING CALCIUM IN SOLUTION FORM

|  | 5 | 6 | 7 | 8 |
|---|---|---|---|---|
| Ethyl Alcohol 200 proof (Denatured SDA 40 B) | 98.0 |  |  |  |
| Water, De-ionized |  | 98 | 99.5 | 99.0 |
| Calcium nitrate |  | 2.0 |  |  |
| Calcium chloride | 2.0 |  | .5 | .5 |
| Calcium Pantothenate |  |  |  | .5 |

Fluoride solutions prepared in accordance with this invention contain an effective amount of fluoride, the fluorides being listed as recited above. Effective amounts range from 0.1% by weight to 5% by weight.

A cream fluoride preparation can be prepared in similar fashion as the calcium creams prepared above.

When a cream is used as a carrier for the fluoride ingredient of this invention, the fluoride ingredient would be first dissolved in the water phase.

The following examples of such fluoride creams are shown in parts per weight: There are four examples numbered 9–12 respectively.

|  | 9 | 10 | 11 | 12 |
|---|---|---|---|---|
| Water Phase |  |  |  |  |
| De ionized water | 79.51 | 81.41 | 79.91 | 72.01 |
| Methylparaben | . | .1 | .1 | .1 |
| Propylene Glycol | 5.00 | 5.0 | 5.0 | 5.0 |
| Glycerin | 3.00 | 3.0 | 3.0 | 3.0 |
| Sodium fluoride | 2.00 | .50 | .10 | 5.0 |
| Stannous fluoride | .50 | .10 | 2.00 | 5.0 |
| Imidazolidinyl Urea | .50 | .5 | .5 | .5 |
| Oil Phase |  |  |  |  |
| Cetearyl Alcohol and Cetearth 20 | 1.5 | 1.5 | 1.5 | 1.5 |
| Cetearyl Alcohol | 1.5 | 1.5 | 1.5 | 1.5 |
| Glycerol Stearate | 1.5 | 1.5 | 1.5 | 1.5 |
| Triceteareth-4 Phosphate | .42 | .42 | .42 | .42 |
| Propylparaben | .20 | .20 | .20 | .20 |
| Myristyl Octanoate | 4.27 | 4.27 | 4.27 | 4.27 |

The preferred fluoride phases of this invention are simple solutions preferably in anhydrous ethyl alcohol. There are four examples in parts per weight numbered 13 through 16 respectively.

|  | 13 | 14 | 15 | 16 |
|---|---|---|---|---|
| De-ionized Water | 99.9 | 97.0 |  |  |
| Ammonium hexafluorophosphate |  |  | .05 | 2.00 |
| Anhydrous Ethyl Alcohol |  |  | 99.95 | 98.00 |
| Stannous fluoride | .10 | 3.0 |  |  |

TEST RESULTS

Two clinical evaluations were made evaluating the effects of treating fingernails with solutions of creams containing calcium followed by application of fluoride. Before any treatment occurred, samples of fingernail were obtained from each subject and assayed for its calcium content.

Methods for the assay of calcium are well known in the art utilizing atomic absorption spectrophotomitry. The method used is generally described by Vellar in an article titled, Composition of Human Nail Substance, *The American Journal of Clinical Nutrition,* Vol. 23, No. 10, October 1970, pp. 1272–1274.

The nails of five healthy subjects were collected before treatment with the calcium and fluoride compositions of this invention. Further samples were collected on a weekly basis for four consecutive weeks. Because of the small sample weights of individual nails, the nails for each week were combined and results are reported for each week for each subject as indicated below.

For this test, the fluoride used was that of Example 16 and the calcium used was that of Example 1. First the calcium cream of Example 1 was brushed onto the nail and rubbed into the nail. Next, the fluoride solution of example 16 was brushed onto the nail and allowed to dry. The process was repeated once daily for the duration of the test. The results were as follows.

| | Calcium Content Initial | Calcium Content After 4 weeks | Percent Change |
|---|---|---|---|
| Subject One | .09 mg/g | .12 mg/g | +33% |
| Subject Two | .49 mg/g | .80 mg/g | +63% |
| Subject Three | .63 mg/g | .66 mg/g | +5% |
| Subject Four | .30 mg/g | .35 mg/g | +17% |
| Subject Five | .41 mg/g | 1.48 mg/g | +309% |

In order to measure nail strength, a platform was used which positions the fingernail over a flattened cylinder. The cylinder creates a gap resulting from the curve of the nail and remains constant from week to week. Since the distance from the nail to the top of the flattened cylinder remains constant, the force required to bend the nail flat against the flattened cylinder can then be easily be measured using a WAGNER force gauge. The gauge indicates the force required to bend the nail a constant distance in grams per square inch.

| | Nail Strength Initial | Nail Strength 4 Weeks | % Change |
|---|---|---|---|
| Subject One | 203 | 320 | +58% |
| Subject Two | 179 | 358 | +100% |
| Subject Three | 213 | 455 | +113% |
| Subject Four | 196 | 345 | +76% |
| Subject Five | 179 | 334 | +86% |

The above listed results demonstrate that even small increases in the calcium content of the nail contribute to meaningful increases in the strength of the fingernail.

While the invention has been described with particular reference to the detailed embodiments, the protection solicited is to be limited only by the terms of the claims which follow.

What is claimed is:

1. A method for treating keratin, said keratin containing a natural amount of calcium, said method comprising the steps of:
    applying a soluble calcium salt to the keratin surface, said calcium salt being dissolved into one member from the group consisting of cosmetically acceptable creams and liquid solvents, the calcium content being large enough when combined with the natural calcium content to increase the total calcium content of the keratin and thus increase the strength thereof;
    thereafter applying a soluble fluoride salt to the keratin surface, said fluoride salt being dissolved into one member of the group consisting of cosmetically acceptable creams and liquid solvents;
    these two salts reacting to precipitate an insoluble calcium fluoride compound within the keratin, the amount of fluoride being large enough after reacting with the calcium salt to cause the said increase in total calcium content of the keratin.

2. A method for increasing the calcium content of fingernail keratin, said method comprising:
    (a) providing a cosmetically acceptable cream or suitable solvent containing a cosmetically acceptable calcium salt dissolved therein providing an amount of calcium sufficient for increasing the calcium content of the fingernail;
    (b) providing a cosmetically acceptable cream or suitable solvent containing a cosmetically acceptable fluoride material dissolved therein sufficient to combine with calcium salt of (a) to provide an increase in the calcium content of the human nail;
    (c) applying the calcium salt of step (c) to the outer surface of the nail and allowing same to dry and penetrate into the nail;
    (d) applying the fluoride composition (b) to the outer surface of the nail and allowing same to dry and penetrate the nail, thereby causing the two applied compositions to react chemically on the said outer nail surface, thus precipitating an insoluble calcium fluoride compound within the nail keratin which increases the total calcium content within the keratin and thus increases the strength of the nail.

3. The method of claim 2 wherein the calcium salt is chosen from the group consisting of calcium acetylsalicylate, calcium ascorbate, calcium chloride, calcium citrate, calcium cyclamate, calcium gluconate, calcium glycerophosphate, calcium 2-ethylbutanoate, calcium methonate, calcium pantothenate, calcium phenosulfonate, calcium propionate, calcium nitrate, calcium sulfate and calcium hydroxide.

4. The method of claim 3 wherein the fluoride is chosen from the group consisting of alkali metal fluorides such as sodium fluoride, lithium fluoride, potassium fluoride, ammonium fluoride, stannous fluoride, zirconium fluoride, nickel fluoride, Sodium monofluorophosphate, lithium monofluorophosphate, potassium monofluorophosphate or ammonium monofluorophosphate.

5. The method of claim 4 wherein the calcium salt content falls within the range of 0.05 to 10 parts by weight.

6. The method of claim 5 wherein the fluoride salt content falls within the range of 0.05 to 3 parts by weight.

7. The method of claim 1 wherein the solvents in the calcium salt class include water, and anhydrous alcohol and the calcium salts include calcium chloride and calcium nitrate.

8. The method of claim 7 wherein the solvents in the fluoride salt class includes anhydrous ethyl alcohol and the fluoride salt includes ammonium hexafluorophosphate.

9. The method of claim 8 wherein the calcium salt content falls within the range of 0.05 to 10 parts by weight and wherein the fluoride salt content falls within the range of 0.05 to 3 parts by weight.

* * * * *